US011161887B2

(12) United States Patent
Völkl et al.

(10) Patent No.: US 11,161,887 B2
(45) Date of Patent: Nov. 2, 2021

(54) UROMODULIN FOR USE IN PREVENTION AND THERAPY OF PATHOLOGICAL CRYSTALLIZATION

(71) Applicant: CHARITÉ UNIVERSITÄTSMEDIZIN BERLIN, Berlin (DE)

(72) Inventors: Jakob Völkl, Berlin (DE); Ioana Alesutan, Berlin (DE); Jürgen Scherberich, Grunwald (DE)

(73) Assignee: CHARITÉ UNIVERSITÄTSMEDIZIN BERLIN, Berlin (DE)

( * ) Notice: Subject to any disclaimer, the term of this patent is extended or adjusted under 35 U.S.C. 154(b) by 0 days.

(21) Appl. No.: 16/488,601

(22) PCT Filed: Feb. 27, 2018

(86) PCT No.: PCT/EP2018/054839
§ 371 (c)(1),
(2) Date: Aug. 26, 2019

(87) PCT Pub. No.: WO2018/158267
PCT Pub. Date: Sep. 7, 2018

(65) Prior Publication Data
US 2020/0010520 A1 Jan. 9, 2020

(30) Foreign Application Priority Data
Feb. 28, 2017 (EP) ..................................... 17158574

(51) Int. Cl.
*A61K 38/16* (2006.01)
*A61P 9/10* (2006.01)
*C07K 14/47* (2006.01)

(52) U.S. Cl.
CPC .............. *C07K 14/473* (2013.01); *A61P 9/10* (2018.01)

(58) Field of Classification Search
CPC ....... A61K 38/1709; A61K 38/16; A61P 9/10; C07K 14/473; C07K 14/47
USPC .......................... 514/1.1, 15.4, 21.2; 530/300
See application file for complete search history.

(56) References Cited

U.S. PATENT DOCUMENTS 4,977,244 A 12/1990 Muchmore et al.
2006/0069068 A1* 3/2006 Kajander ............. A61K 31/663
514/89

FOREIGN PATENT DOCUMENTS

WO 00/15772 3/2000
WO 2016/069234 5/2016

OTHER PUBLICATIONS

Peripheral Arterial Disease from Merck Manual, pp. 1-6. Accessed Oct. 19, 2020. (Year: 2020).*
Nonatheromatous Arteriosclerosis from Merck Manual, pp. 1-2. Accessed Oct. 19, 2020. (Year: 2020).*
Atherosclerosis from Merck Manual, pp. 1-12. Accessed Oct. 19, 2020. (Year: 2020).*
Rudinger J, "Characteristics of the amino acids as components of a peptide hormone sequence," Peptide Hormones, JA Parsons Edition, University Park Press, Jun. 1976, pp. 1-7. (Year: 1976).*
"Designing Custom Peptides," from SIGMA Genosys, pp. 1-2. Accessed Dec. 16, 2004. (Year: 2004).*
Berendsen HJC, "A Glimpse of the Holy Grail?" Science, 1998, 282: 642-643. (Year: 1998).*
Voet D, Voet JG, Biochemistry, Second Edition, John Wiley & Sons, Inc., 1995, pp. 235-241. (Year: 1995).*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495. (Year: 1994).*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386. (Year: 2002).*
Adessi et al, "Converting a Peptide into a Drug: Strategies to Improve Stability and Bioavailability," Current Medical Chemistry, 2002 , 9: 963-978. (Year: 2002).*
Peptide Design from ThermoFisher Scientific, pp. 1-9. Accessed Jan. 23, 2019. (Year: 2019).*
Yampolsky et al., "The Exchangeability of Amino Acids in Proteins," Genetics, 2005, 170: 1459-1472. (Year: 2005).*
Rampoldi et al, "THe redicsovery of uromodulin (Tamm-Horsfall protein): from tubulointerstitial nephropathy to chronic kidney disease," Kidney International, 2011, 80: 338-347. (Year: 2011).*
UniProt P07911, pp. 1-27. Integrated into UniProtKB/Swiss-Prot on Aug. 1, 1988. (Year: 1988).*
Schlieper Georg et al: "Inhibitors of calcification in blood and urine.", Seminars in Dialysis, vol. 20, No. 2, Mar. 2007, pp. 113-121.
Liu Yan et al: "Progressive renal papillary calcification and ureteral stone formation in mice deficient for Tamm-Horsfall protein", American Journal of Physiology-Renal Physiology, vol. 299, No. 3, Sep. 2010, pp. F469-F478.
Jian Liguo et al: "Functional analysis of UMOD gene and its effect on inflammatory cytokines in serum of essential hypertension patients", International Journal of Clinical and Experimental Pathology, vol. 8, No. 9, 2015, pp. 11356-11363.

(Continued)

*Primary Examiner* — Julie Ha
(74) *Attorney, Agent, or Firm* — JMB Davis Ben-David

(57) ABSTRACT

Described herein is the use of a uromodulin polypeptide in prevention or therapy of vascular calcification or a disease caused by, or related to, vascular calcification, particularly vascular calcification in chronic kidney disease, in diabetes, in aging and in atherosclerosis.

9 Claims, 8 Drawing Sheets
Specification includes a Sequence Listing.

(56) References Cited

OTHER PUBLICATIONS

Suzuki Taihei et al.: "Uromodulin Exerts Potent Preventive and Therapeutic Effects In WKY Rats With AntiGBM Glomerulonephritis Via IL6 Activation", Nephrology Dialysis Transplantation, vol. 31, No. Suppl. 1, May 2016, p. 369.
Oberoi Raghav et al: "Targeting Tumor Necrosis Factor-alpha with Adalimumab: Effects on Endothelial Activation and Monocyte Adhesion", PLOS One, vol. 11, No. 7, Jul. 2016.
Hamirani Y S et al: "Markers of inflammation and coronary artery calcification: A systematic review", Atherosclerosis, Elsevier, Amsterdam, NL, vol. 201, No. 1, Nov. 1, 2008, pp. 1-7.
Shao Jian-Su et al: "Inflammation and the Osteogenic Regulation of Vascular Calcification of Review and Perspective", Hypertension (Baltimore), vol. 55, No. 3, Mar. 2010, pp. 579-592.
Bjornstad Petter et al: "Uromodulin Improves Prediction of Coronary Atherosclerosis over 12 Years in Adults with Type 1 Diabetes", Diabetes, vol. 66, No. Suppl. 1, Jun. 1, 2017, p. A1.

\* cited by examiner

Fig. 4 (contd)
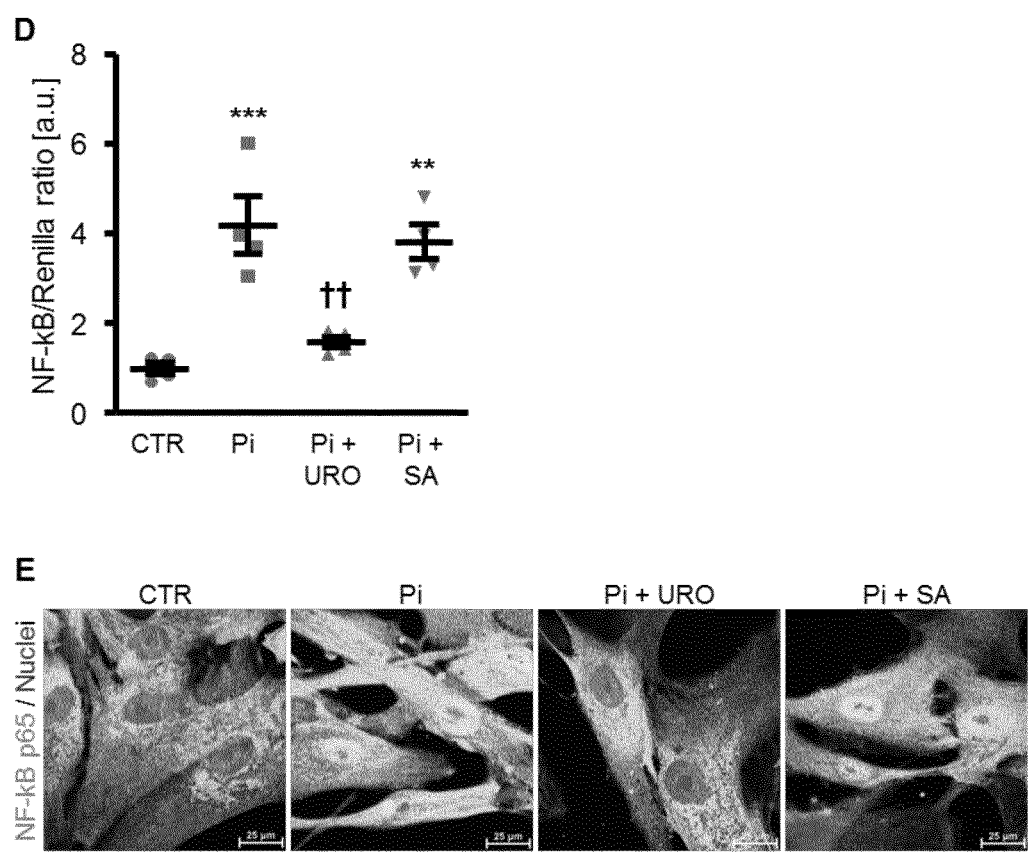

SEQUENCE LISTING

<160> NUMBER OF SEQ ID NOS: 15

<210> SEQ ID NO 1
<211> LENGTH: 640
<212> TYPE: PRT
<213> ORGANISM: homo sapiens

<400> SEQUENCE: 1

Met Gly Gln Pro Ser Leu Thr Trp Met Leu Met Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

```
Gly Phe Arg Leu Ser Pro Gly Leu Gly Cys Thr Asp Val Asp Glu Cys
                100                 105                 110
Ala Glu Pro Gly Leu Ser His Cys His Ala Leu Ala Thr Cys Val Asn
            115                 120                 125
Val Val Gly Ser Tyr Leu Cys Val Cys Pro Ala Gly Tyr Arg Gly Asp
        130                 135                 140
Gly Trp His Cys Glu Cys Ser Pro Gly Ser Cys Gly Pro Gly Leu Asp
145                 150                 155                 160
Cys Val Pro Glu Gly Asp Ala Leu Val Cys Ala Asp Pro Cys Gln Ala
                165                 170                 175
His Arg Thr Leu Asp Glu Tyr Trp Arg Ser Thr Glu Tyr Gly Glu Gly
            180                 185                 190
Tyr Ala Cys Asp Thr Asp Leu Arg Gly Trp Tyr Arg Phe Val Gly Gln
        195                 200                 205
Gly Gly Ala Arg Met Ala Glu Thr Cys Val Pro Val Leu Arg Cys Asn
    210                 215                 220
Thr Ala Ala Pro Met Trp Leu Asn Gly Thr His Pro Ser Ser Asp Glu
225                 230                 235                 240
Gly Ile Val Ser Arg Lys Ala Cys Ala His Trp Ser Gly His Cys Cys
                245                 250                 255
Leu Trp Asp Ala Ser Val Gln Val Lys Ala Cys Ala Gly Gly Tyr Tyr
            260                 265                 270
Val Tyr Asn Leu Thr Ala Pro Pro Glu Cys His Leu Ala Tyr Cys Thr
        275                 280                 285
Asp Pro Ser Ser Val Glu Gly Thr Cys Glu Cys Ser Ile Asp Glu
    290                 295                 300
Asp Cys Lys Ser Asn Asn Gly Arg Trp His Cys Gln Cys Lys Gln Asp
305                 310                 315                 320
Phe Asn Ile Thr Asp Ile Ser Leu Leu Glu His Arg Leu Glu Cys Gly
                325                 330                 335
Ala Asn Asp Met Lys Val Ser Leu Gly Lys Cys Gln Leu Lys Ser Leu
            340                 345                 350
Gly Phe Asp Lys Val Phe Met Tyr Leu Ser Asp Ser Arg Cys Ser Gly
        355                 360                 365
Phe Asn Asp Arg Asp Asn Arg Asp Trp Val Ser Val Val Thr Pro Ala
    370                 375                 380
Arg Asp Gly Pro Cys Gly Thr Val Leu Thr Arg Asn Glu Thr His Ala
385                 390                 395                 400
Thr Tyr Ser Asn Thr Leu Tyr Leu Ala Asp Glu Ile Ile Ile Arg Asp
                405                 410                 415
Leu Asn Ile Lys Ile Asn Phe Ala Cys Ser Tyr Pro Leu Asp Met Lys
            420                 425                 430
Val Ser Leu Lys Thr Ala Leu Gln Pro Met Val Ser Ala Leu Asn Ile
        435                 440                 445
Arg Val Gly Gly Thr Gly Met Phe Thr Val Arg Met Ala Leu Phe Gln
    450                 455                 460
Thr Pro Ser Tyr Thr Gln Pro Tyr Gln Gly Ser Ser Val Thr Leu Ser
465                 470                 475                 480
Thr Glu Ala Phe Leu Tyr Val Gly Thr Met Leu Asp Gly Gly Asp Leu
                485                 490                 495
Ser Arg Phe Ala Leu Leu Met Thr Asn Cys Tyr Ala Thr Pro Ser Ser
            500                 505                 510
Asn Ala Thr Asp Pro Leu Lys Tyr Phe Ile Ile Gln Asp Arg Cys Pro
```

```
             515                 520                 525
His Thr Arg Asp Ser Thr Ile Gln Val Val Glu Asn Gly Glu Ser Ser
    530                 535                 540

Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
                565                 570                 575

Lys Cys Lys Pro Thr Cys Ser Gly Thr Arg Phe Arg Ser Gly Ser Val
                580                 585                 590

Ile Asp Gln Ser Arg Val Leu Asn Leu Gly Pro Ile Thr Arg Lys Gly
                595                 600                 605

Val Gln Ala Thr Val Ser Arg Ala Phe Ser Ser Leu Gly Leu Leu Lys
            610                 615                 620

Val Trp Leu Pro Leu Leu Leu Ser Ala Thr Leu Thr Leu Thr Phe Gln
625                 630                 635                 640

<210> SEQ ID NO 2
<211> LENGTH: 21
<212> TYPE: DNA
<213> ORGANISM: homo sapiens

<400> SEQUENCE: 2
gggactggta ctcagacaac g                                              21

<210> SEQ ID NO 3
<211> LENGTH: 21
<212> TYPE: DNA
<213> ORGANISM: homo sapiens

<400> SEQUENCE: 3
gtaggcgatg tccttacagc c                                              21

<210> SEQ ID NO 4
<211> LENGTH: 23
<212> TYPE: DNA
<213> ORGANISM: homo sapiens

<400> SEQUENCE: 4
gccttccact ctcagtaaga aga                                            23

<210> SEQ ID NO 5
<211> LENGTH: 20
<212> TYPE: DNA
<213> ORGANISM: Homo sapiens

<400> SEQUENCE: 5
gcctggggtc tgaaaaaggg                                                20

<210> SEQ ID NO 6
<211> LENGTH: 20
<212> TYPE: DNA
<213> ORGANISM: Homo sapiens

<400> SEQUENCE: 6
gagtcaacgg atttggtcgt                                                20

<210> SEQ ID NO 7
<211> LENGTH: 20
<212> TYPE: DNA
<213> ORGANISM: Homo sapiens
```

```
<400> SEQUENCE: 7
gacaagcttc ccgttctcag                                               20

<210> SEQ ID NO 8
<211> LENGTH: 22
<212> TYPE: DNA
<213> ORGANISM: Mus musculus

<400> SEQUENCE: 8
ttgtgccaga gaaagagaga ga                                            22

<210> SEQ ID NO 9
<211> LENGTH: 22
<212> TYPE: DNA
<213> ORGANISM: Mus musculus

<400> SEQUENCE: 9
gtttcagggc atttttcaag gt                                            22

<210> SEQ ID NO 10
<211> LENGTH: 23
<212> TYPE: DNA
<213> ORGANISM: Mus musculus

<400> SEQUENCE: 10
agagtcagat tacagatccc agg                                           23

<210> SEQ ID NO 11
<211> LENGTH: 22
<212> TYPE: DNA
<213> ORGANISM: Mus musculus

<400> SEQUENCE: 11 aggagggta agactggtca ta                                             22

<210> SEQ ID NO 12
<211> LENGTH: 21
<212> TYPE: DNA
<213> ORGANISM: Mus musculus

<400> SEQUENCE: 12
aggtcggtgt gaacggattt g                                             21

<210> SEQ ID NO 13
<211> LENGTH: 23
<212> TYPE: DNA
<213> ORGANISM: Mus musculus

<400> SEQUENCE: 13
tgtagaccat gtagttgagg tca                                           23

<210> SEQ ID NO 14
<211> LENGTH: 19
<212> TYPE: DNA
<213> ORGANISM: Mus musculus

<400> SEQUENCE: 14
ggcacccatg tggctcaat                                                19

<210> SEQ ID NO 15
<211> LENGTH: 21
<212> TYPE: DNA
<213> ORGANISM: Mus musculus
```

```
<400> SEQUENCE: 15
gggcgctgtc aagttgtaaa t                                                  21
```

UROMODULIN FOR USE IN PREVENTION AND THERAPY OF PATHOLOGICAL CRYSTALLIZATION

CROSS-REFERENCE TO RELATED APPLICATIONS

This is the U.S. National Stage of International Patent Application No. PCT/EP2018/054839 filed on Feb. 27, 2018, which was published in English under PCT Article 21(2), and which in turn claims the benefit of European Patent Application No. 17158574.8 filed on Feb. 28, 2017.

The present invention relates to the use of uromodulin and related polypeptide derivatives for treating or preventing conditions related to pathological calcium-phosphate crystallization.

DESCRIPTION

Vascular calcification predicts cardiovascular mortality. The presence of vascular calcification is associated with a 3-4 fold increased risk of cardiovascular events and mortality and has been suggested as an underlying culprit causing the high cardiovascular mortality in the western world. In the general population, abdominal aortic calcification is associated with cardiovascular events and death. The most extensive calcifications are observed in patients with chronic kidney disease, and these calcifications have been suggested to cause the extreme cardiovascular mortality in these patients. The calcification in patients with renal failure are strongly promoted by phosphate, which has been recognized as a vascular toxin also in patients without overt renal failure.

Vascular calcification has been recognized as an active process governed by vascular smooth muscle cells, which dedifferentiate and exhibit a phenotype of osteoblast-like cells under pathological stress. The osteoblastic phenotype is characterized by expression of osteo-/chondroblastic transcription factors, such as CBFA1/RUNX2, MSX2 and alkaline phosphatase (ALPL). These osteoblastic transformed cells actively promote soft tissue calcification, predominantly in the arteries. The reprogramming is fostered by inflammatory cytokines and is associated with a generalized inflammation. No therapeutic agent is clinically available to hinder the progression of vascular calcification.

Until now, no treatment is available to clinicians to effectively prevent the onset of vascular calcification or hinder its progression.

Uromodulin (Uniprot Identifier P07911, SEQ ID NO 001), also named Tamm-Horsfall glycoprotein (THP), is a protein produced mainly in the kidney and secreted into the urine. As one of the most abundant proteins in the urine, it serves various functions, including the regulation of salt balance. Recent research showed that uromodulin is also secreted into the blood and reaches the systemic circulation with mean uromodulin plasma levels of around 200 ng/ml in healthy subjects.

Most importantly, during renal failure, uromodulin levels decline with disease progression and have been suggested as a marker for remaining renal function. However, no information has been available for any functional effects of uromodulin in the systemic circulation, prior to the present specification.

Based on the properties of uromodulin, the inventors investigated a functional role for uromodulin, which may explain its presence in the systemic circulation. We have found that uromodulin is a most powerful inhibitor of vascular calcification.

Based on the above-mentioned state of the art, the objective of the present invention is to provide means and methods for the prevention and treatment of vascular calcification and its associated symptoms and clinical consequences. This objective is attained by the claims of the present specification.

TERMS AND DEFINITIONS

The term uromodulin in the context of the present specification relates to the protein of SEQ ID NO 001

```
SEQ ID NO 001: human uromodulin isoform 1
MGQPSLTWMLMVVVASWFITTAATDTSEARWCSECHSNATCTEDEAVTTC

TCQEGFTGDGLTCVDLDECAIPGAHNCSANSSCVNTPGSFSCVCPEGFRL

SPGLGCTDVDECAEPGLSHCHALATCVNVVGSYLCVCPAGYRGDGWHCEC

SPGSCGPGLDCVPEGDALVCADPCQAHRTLDEYWRSTEYGEGYACDTDLR

GWYRFVGQGGARMAETCVPVLRCNTAAPMWLNGTHPSSDEGIVSRKACAH

WSGHCCLWDASVQVKACAGGYYVYNLTAPPECHLAYCTDPSSVEGTCEEC

SIDEDCKSNNGRWHCQCKQDFNITDISLLEHRLECGANDMKVSLGKCQLK

SLGFDKVFMYLSDSRCSGFNDRDNRDWVSVVTPARDGPCGTVLTRNETHA

TYSNTLYLADEIIIRDLNIKINFACSYPLDMKVSLKTALQPMVSALNIRV

GGTGMFTVRMALFQTPSYTQPYQGSSVTLSTEAFLYVGTMLDGGDLSRFA

LLMTNCYATPSSNATDPLKYFIIQDRCPHTRDSTIQVVENGESSQGRFSV

QMFRFAGNYDLVYLHCEVYLCDTMNEKCKPTCSGTRFRSGSVIDQSRVLN

LGPITRKGVQATVSRAFSSLGLLKVWLPLLLSATLTLTFQ
```

The term biological activity of the uromodulin polypeptide of SEQ ID NO 001 in the context of the present specification relates to the activity measured in the assay shown in FIG. 1.

Amino acid sequences are given from amino to carboxyl terminus. Capital letters for sequence positions refer to L-amino acids in the one-letter code (Stryer, Biochemistry, 3$^{rd}$ ed. p. 21).

In the context of the present specification, the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information.

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively.

As used herein, the term "treating" or "treatment" of any disease or disorder (e.g. vascular calcification or any of its associated pathologies and downstream deleterious effects) refers in one embodiment, to ameliorating the disease or disorder (e.g. slowing or arresting or reducing the development of the disease or at least one of the clinical symptoms thereof). In another embodiment, "treating" or "treatment" refers to alleviating or ameliorating at least one physical parameter including those, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described herein below.

A first aspect of the invention relates to a uromodulin polypeptide for use in prevention or therapy of vascular calcification or a disease caused by, or related to, vascular calcification, particularly vascular calcification in chronic kidney disease, in diabetes, in aging and in atherosclerosis.

In certain embodiments, the uromodulin polypeptide for use in prevention or therapy of vascular calcification comprises or essentially consists of the polypeptide sequence of SEQ ID NO 001.

In certain embodiments, the uromodulin polypeptide for use in prevention or therapy of vascular calcification
  a. comprises or essentially consists of an amino acid sequence characterized by more than (≥) 85% identity, particularly ≥90% identity, even more particularly ≥92%, ≥94%, ≥95%, ≥96, ≥97%, ≥98%, or ≥99% identity to the polypeptide sequence of SEQ ID NO 001, and
  b. is characterized by at least 85% biological activity of the uromodulin polypeptide of SEQ ID NO 001.

In certain embodiments, the uromodulin polypeptide for use in prevention or therapy of vascular calcification is a recombinant peptide.

In certain embodiments, the uromodulin polypeptide is provided for use in prevention or therapy of vascular calcification, wherein the disease is characterized by a peripheral uromodulin level below 180 ng/ml, particularly a peripheral uromodulin level below 160 ng/ml, even more particularly a peripheral uromodulin level below 125 ng/ml, particularly below 110 ng/ml, even more particularly below 100 ng/ml, 80 ng/ml or 60 ng/ml.

Another aspect of the invention relates to a uromodulin polypeptide for use in prevention or therapy of vascular inflammation, particularly wherein the vascular inflammation is associated with vascular calcification.

In certain embodiments of this aspect of the invention, the uromodulin peptide for use in prevention or therapy of vascular inflammation comprises or essentially consists of the polypeptide sequence of SEQ ID NO 001.

In certain embodiments of this aspect of the invention, the uromodulin peptide for use in prevention or therapy of vascular inflammation
  a. comprises or essentially consists of an amino acid sequence characterized by more than (≥) 85% identity, particularly ≥90% identity, even more particularly ≥92%, ≥94%, ≥95%, ≥96, ≥97%, ≥98%, or ≥99% identity to the polypeptide sequence of SEQ ID NO 001, and
  b. is characterized by at least 85% biological activity of the uromodulin polypeptide of SEQ ID NO 001.

The invention further relates to a method for treatment of vascular calcification or a condition related to, or caused by, vascular calcification, in a patient, comprising administering to the patient an effective dose of a uromodulin polypeptide, wherein the uromodulin peptide comprises or essentially consists of the polypeptide sequence of SEQ ID NO 001, or wherein the uromodulin peptide
  a. comprises or essentially consists of an amino acid sequence characterized by more than (≥) 85% identity, particularly ≥90% identity, even more particularly ≥92%, ≥94%, ≥95%, ≥96, ≥97%, ≥98%, or ≥99% identity to the polypeptide sequence of SEQ ID NO 001, and
  b. is characterized by at least 85% biological activity of the uromodulin polypeptide of SEQ ID NO 001.

The invention also relates to a pharmaceutical composition comprising a uromodulin polypeptide as specified above, for use in prevention or therapy of vascular calcification.

The invention also relates to a method for making a pharmaceutical for use in prevention or therapy of vascular calcification, the method comprising the use of a uromodulin polypeptide as specified herein.

Conditions related to pathological calcium-phosphate crystallization for which the polypeptides of the present invention are particularly useful include vascular calcification, particularly vascular calcification in chronic kidney disease, in diabetes, in aging and in atherosclerosis.

The polypeptides of the present invention are furthermore particularly useful to mitigate calcification-associated diseases such as cardiac dysfunction and hypertrophy, heart failure, stroke and renal failure, hypertension, organ fibrosis, peripheral artery disease and calciphylaxis.

The uromodulin polypeptide for use as specified herein may be modified to enhance its stability, prevent aggregation or otherwise render the polypeptide more pharmaceutically available to the patient. Modifications include microparticle encapsulation, for example in biodegradable microspheres or nanospheres. The polypeptide may additionally or alternatively be modified with polyethylene glycol (PEG) moieties ("pegylated"), or may be part of a fusion protein comprising a polypeptide chain known to impart stability on the therapeutic protein in the bloodstream, such as the Fc chain of the IgG antibody.

Similarly, a method or treating vascular calcification in a patient in need thereof is within the scope of the present invention, comprising administering to the patient a uromodulin polypeptide according to the above description.

Similarly, a dosage form for the prevention or treatment of vascular calcification is provided, comprising a uromodulin polypeptide according to one of the above aspects of the invention.

Dosage forms may be for parenteral administration, such as subcutaneous, intravenous, intrahepatic or intramuscular injection forms. Optionally, a pharmaceutically acceptable carrier and/or excipient may be present.

Another aspect of the invention relates to a nucleic acid expression system comprising a nucleic acid sequence, wherein said nucleic acid sequence encodes a polypeptide comprising an amino acid sequence characterized by more than (≥) 85% identity, particularly ≥90% identity, even more particularly ≥92%, ≥94%, ≥95%, ≥96, ≥97%, ≥98%, or ≥99% identity to the polypeptide sequence of SEQ ID NO 001, wherein said polypeptide is characterized by at least 85% biological activity of the uromodulin polypeptide of SEQ ID NO 001, for use in prevention or therapy of vascular calcification and/or vascular inflammation.

In certain embodiments, the nucleic acid sequence is under control of a promoter operable in a human cell, for use in prevention or therapy of vascular calcification and/or vascular inflammation. In certain embodiments, said promoter is operable in a vascular epithelial cell.

In certain embodiments, the promoter is constitutively active. In certain other embodiments, the promoter is inducible, for example by a small molecule pharmaceutical.

In certain embodiments, the nucleic acid system is a virus, particularly a virus selected from adenovirus, adeno-associated virus, and herpesvirus, for use in prevention or therapy of vascular calcification and/or vascular inflammation.

Wherever alternatives for single separable features are laid out herein as "embodiments", it is to be understood that such alternatives may be combined freely to form discrete embodiments of the invention disclosed herein.

The invention is further illustrated by the following examples and figures from which further embodiments and advantages can be drawn. These examples are meant to illustrate the invention but not to limit its scope.

MATERIALS AND METHODS

Figure 1:
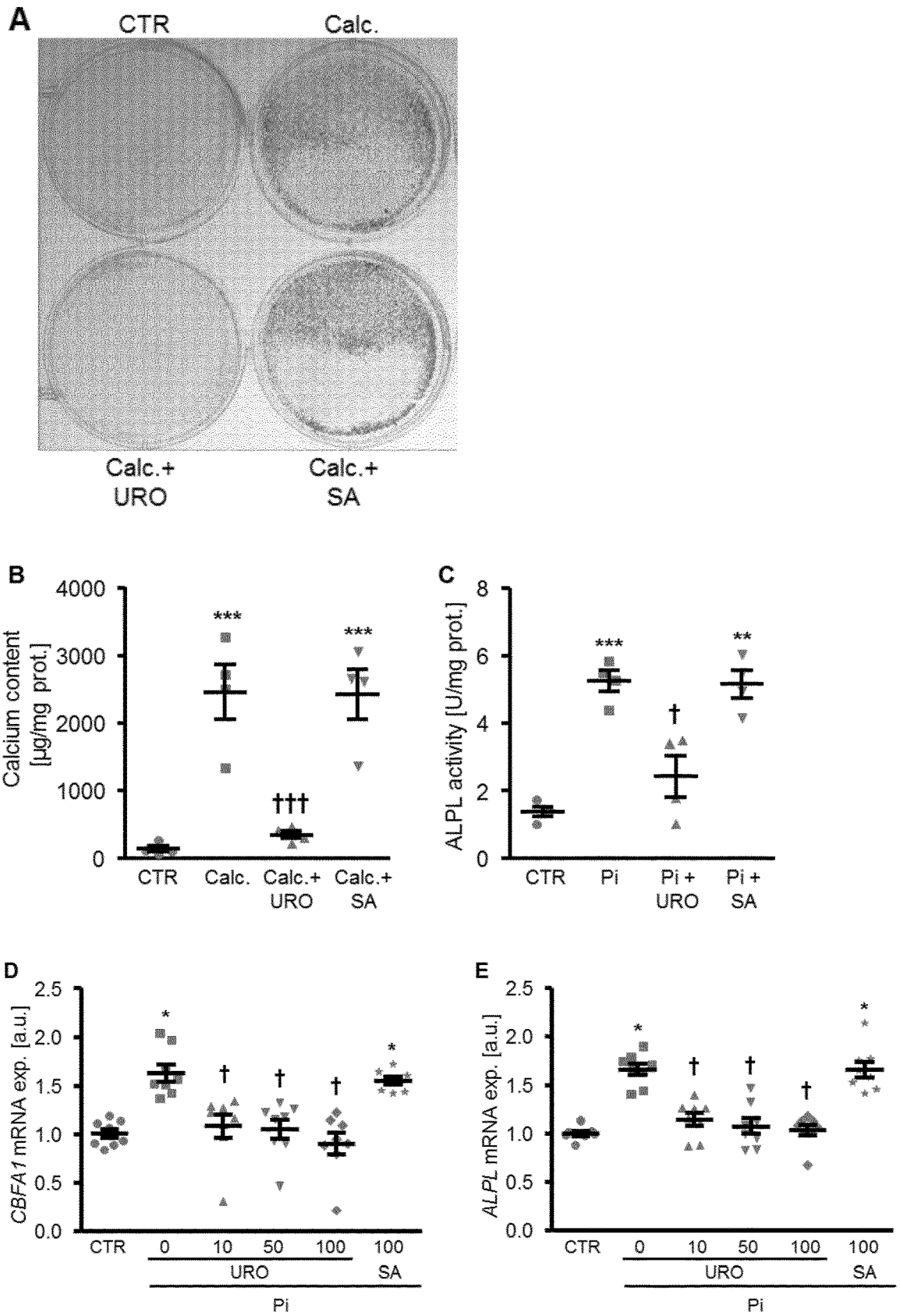
FIG. 1 A. Representative original images showing Alizarin red staining in HAoSMCs following treatment for 11 days with control or with calcification medium (Calc., 10 mM β-glycerophosphate+1.5 mM $CaCl_2$) without or with additional treatment with 100 ng/ml native human uromodulin (URO) or 100 ng/ml serum albumin (SA). Images are representative for six independent experiments. The calcified areas are shown as red staining. B. Scatter dot plots and arithmetic means±SEM (n=4, μg/mg protein) of calcium content in HAoSMCs following treatment for 11 days with control or with calcification medium (Calc., 10 mM β-glycerophosphate+1.5 mM $CaCl_2$)) without or with additional treatment with 100 ng/ml native human uromodulin (URO) or 100 ng/ml serum albumin (SA). C. Scatter dot plots and arithmetic means±SEM (n=4, U/mg protein) of alkaline phosphatase activity in HAoSMCs following treatment for 7 days with control or with 2 mM β-glycerophosphate (Pi) without or with additional treatment with 100 ng/ml native human uromodulin (URO) or 100 ng/ml serum albumin (SA). D,E. Scatter dot plots and arithmetic means±SEM (n=8; arbitrary units, a.u.) of CBFA1 (D) and ALPL (E) relative mRNA expression in HAoSMCs following treatment for 24 hours with control or with 2 mM β-glycerophosphate (Pi) without or with additional treatment with indicated concentrations of native human uromodulin (URO, 0-100 ng/ml) or 100 ng/ml serum albumin (SA). *($p<0.05$), ($p<0.01$), *($p<0.001$) statistically significant vs. control treated HAoSMCs; †($p<0.05$), †††($p<0.001$) statistically significant vs. HAoSMCs treated with Calc./Pi alone.

Cell Culture of Primary Human Aortic Smooth Muscle Cells

Primary human aortic smooth muscle cells (HAoSMCs) commercially obtained from Thermo Fisher Scientific were cultured in Waymouth's MB 752/1 medium and Ham's F-12 nutrient mixture (1:1 ratio, Thermo Fisher Scientific) supplemented with 10% FBS (Thermo Fisher Scientific), 100 U/ml penicillin and 100 µg/ml streptomycin (Thermo Fisher Scientific). The cells were grown to confluence and used in all experiments from passages 4 to 11. At confluence, HAoSMCs were detached using Trypsin/EDTA solution (Thermo Fisher Scientific) and cultured into 6-well plates or 4-well chamber slides (BD Biostatus) for 24 hours prior to treatment. HAoSMCs were treated for the indicated time with 2 mM β-glycerophosphate (Sigma Aldrich), 5 µg/ml hydroxyapatite nanoparticles (Sigma-Aldrich), 0-100 ng/ml native human uromodulin (BBI solutions), 100 ng/ml recombinant human uromodulin (Origene), 100 ng/ml bovine serum albumin (Sigma Aldrich), 1:5000 dilution of mouse monoclonal antibody anti-human uromodulin (Euroimmun) or mouse IgG as control (Santa Cruz Biotechnology), 10 ng/ml human TNFα (stock in PBS, R&D Systems) and 10 ng/ml human IL-1β (stock in PBS/0.1% BSA, R&D Systems). Equal amounts of vehicle were used as control. HAoSMCs were serum starved for 24 hours prior to treatment for 24 hours with 15% uremic serum from hemodialysis patients (uremic serum, US) or control serum from matched healthy individuals (normal serum, NS). Treatment for 11 days with 10 mM β-glycerophosphate and 1.5 mM $CaCl_2$ (Sigma-Aldrich) were used as calcification media for the calcium deposition quantification and for Alizarin Red staining. Fresh media with agents were added every 2-3 days.

Cell Culture of MOVAS Cells

MOVAS cells, a mouse aortic smooth muscle cell line, commercially obtained from ATCC were cultured in DMEM high glucose medium (Thermo Fisher Scientific) supplemented with 10% FBS (Thermo Fisher Scientific) and 0.2 mg/ml G-418 (Thermo Fisher Scientific). At confluence, MOVAS cells were detached using Trypsin/EDTA solution (Thermo Fisher Scientific) and cultured into 6-well plates for 24 hours prior to treatment. MOVAS cells were transfected with 2 µg DNA encoding mouse uromodulin in pCMV6Kan/Neo vector (Origene) or empty vector as control (Origene) using X-tremeGENE HP DNA transfection reagent (Roche Applied Science) according to the manufacturer's protocol. Transfection efficiency was determined by quantitative RT-PCR. MOVAS cells were treated for the indicated time with 2 mM β-glycerophosphate (Sigma Aldrich), 100 ng/ml recombinant mouse uromodulin (Creative BioMart) or 100 ng/ml bovine serum albumin (Sigma Aldrich). Treatment for 11 days with 10 mM β-glycerophosphate and 1.5 mM $CaCl_2$ (Sigma-Aldrich) were used as calcification media for the calcium deposition quantification. Fresh media with agents were added every 2-3 days.

Animal Experiments

All animal experiments were conducted according to the recommendations of the Guide for Care and Use of Laboratory Animals of the National Institutes of Health as well as the German law for the welfare of animals and were approved by local authorities. Generation of AAV8 pseudotyped vectors containing mouse uromodulin or a GFP control was performed using standard procedures. AAVs ($10^{12}$ vg/mouse) were injected intravenously into C57BL/6 mice. The mice were subsequently injected with vehicle or 400000 IU/kg BW of cholecalciferol (Sigma-Aldrich) subcutaneously for three days. After six days, blood was collected by retroorbital puncture. Mice were sacrificed by cervical dislocation under inhalative isoflurane anaesthesia and aortic tissues were rapidly collected and snap-frozen. Plasma concentrations of phosphate and calcium were measured by QuantiChrom Phosphate assay kit and QuantiChrom Calcium assay kit, respectively (BioAssay Systems).

Calcification Analysis

The quantification of aortic arch calcification was performed by incubation of the tissues overnight at 37° C. in 0.6 M HCl. Cells were decalcified for 24 hours at 4° C. in 0.6 M HCl. Calcium content was determined by using QuantiChrom Calcium assay kit (BioAssay Systems) according to the manufacturer's protocol. Tissues or cells were lysed with 0.1 M NaOH/0.1% SDS and total protein concentration was measured by the Bradford assay (Bio-Rad Laboratories). The calcium content was normalized to total protein concentration. To visualize calcium deposition, HAoSMCs were fixed with 4% paraformaldehyde and stained with 2% Alizarin Red (pH 4.5). The calcified areas are shown as red staining.

Alkaline Phosphatase (ALPL) Activity Assay

ALPL activity in the whole cell extract was determined using the ALPL colorimetric assay kit (Abcam) according to the manufacturer's protocol. ALPL activity was normalized to total protein concentration as measured by the Bradford assay (Bio-Rad Laboratories).

Luciferase Assay

HAoSMCs were transfected for 48 hours with 1 μg DNA mixture of NF-kB-responsive luciferase construct and a constitutively expressing Renilla construct (40:1 ratio, Qiagen) as control for transfection efficiency using X-tremeGENE HP DNA transfection reagent (Roche Applied Science) according to the manufacturer's protocol. After the incubation period, HAoSMCs were lysed with Passive Lysis Buffer (Promega) and assayed for transcriptional activity using Dual-Luciferase Reporter Assay (Promega) and a luminometer (Victor 2 plate reader, Perkin Elmer) according to the manufacturer's protocol. Results are expressed as the ratio of NF-kB Firefly-Luciferase to Renilla-Luciferase (relative light units) normalized to control treated HAoSMCs.

Quantitative RT-PCR

Total RNA was isolated from murine aortic tissues, HAoSMCs or MOVAS cells by using Trifast Reagent (Peqlab) according to the manufacturer's instructions. Reverse transcription of 2 μg RNA was performed using oligo(dT)$_{12-18}$ primers (Thermo Fisher Scientific) and SuperScript III Reverse Transcriptase (Thermo Fisher Scientific). Quantitative RT-PCR was performed with the iCycler iQ™ Real-Time PCR Detection System (Bio-Rad Laboratories) and iQ™ Sybr Green Supermix (Bio-Rad Laboratories) according to the manufacturer's instructions. The following human primers were used (Thermo Fisher Scientific, 5'-3' orientation):

```
                                        (SEQ ID NO 002)
ALPL fw:      GGGACTGGTACTCAGACAACG;

(SEQ ID NO 003)
ALPL rev:     GTAGGCGATGTCCTTACAGCC;

(SEQ ID NO 004)
CBFA1 fw:     GCCTTCCACTCTCAGTAAGAAGA;

(SEQ ID NO 005)
CBFA1 rev:    GCCTGGGGTCTGAAAAAGGG;

(SEQ ID NO 006)
GAPDH fw:     GAGTCAACGGATTTGGTCGT;

(SEQ ID NO 007)
GAPDH rev:    GACAAGCTTCCCGTTCTCAG.
```

The following mouse primers were used (Thermo Fisher Scientific, 5'-3' orientation):

```
                                        (SEQ ID NO 008)
AlpI fw:      TTGTGCCAGAGAAAGAGAGAGA;

(SEQ ID NO 009)
AlpI rev:     GTTTCAGGGCATTTTTCAAGGT;

(SEQ ID NO 010)
Cbfa1 fw:     AGAGTCAGATTACAGATCCCAGG;

(SEQ ID NO 011)
Cbfa1 rev:    AGGAGGGGTAAGACTGGTCATA;

(SEQ ID NO 012)
Gapdh fw:     AGGTCGGTGTGAACGGATTTG;

(SEQ ID NO 013)
Gapdh rev:    TGTAGACCATGTAGTTGAGGTCA;

(SEQ ID NO 014)
Umod fw:      GGCACCCATGTGGCTCAAT;

(SEQ ID NO 015)
Umod rev:     GGGCGCTGTCAAGTTGTAAAT.
```

The specificity of the PCR products was confirmed by analysis of the melting curves. All PCRs were performed in duplicate and relative mRNA fold changes were calculated by the $2^{-\Delta\Delta ct}$ method using GAPDH as internal reference. For animal experiments, relative mRNA fold changes were calculated to a control mouse receiving vehicle only.

Immunostaining and Confocal Microscopy

HAoSMCs cultured onto four-well chamber slides (BD Biostatus) were fixed with ice-cold 100% methanol for 10 min at room temperature. To reduce non-specific background staining, slides were incubated with 5% normal goat serum in PBS/0.1% Triton-X100 for 1 hour at room temperature. Cells were incubated overnight at 4° C. with primary rabbit polyclonal anti-NF-kB p65 antibody (diluted 1:50, Santa Cruz Biotechnology) and then with goat anti-rabbit Alexa488-conjugated antibody (diluted 1:1000, Thermo Fisher Scientific) for 1 hour at room temperature. Nuclei were stained using DRAQ5 dye (diluted 1:1000, Biostatus) for 10 min at room temperature. The slides were mounted with Prolong Gold antifade reagent (Thermo Fisher Scientific). Images were collected with a confocal imaging system (A1Rsi+, Nikon Instruments) using a 60× (Oil), 1.4NA objective. Confocal images are representative for three independent experiments. Negative controls were carried out simultaneously with all experiments by omitting incubation with primary antibody.

Immunoprecipitation and Western Blot Analysis

Immunoprecipitation of uromodulin from human serum was performed by using Pierce Direct IP kit (Thermo Fisher Scientific) according to the manufacturer's instructions. Coupling of 6 μl mouse monoclonal anti-human uromodulin antibody (Euroimmun) or mouse IgG as control (Santa Cruz Biotechnology) to the AminoLink Plus coupling resin (Thermo Fisher Scientific) was performed for 2 hours at RT. Human serum (2 mg proteins) from hemodialysis patients before dialysis (CKD) and from healthy volunteers (CTR) was incubated with the immobilized antibody/control to form the immune complex overnight at 4° C. on a rotator. Then, immune complexes were washed to remove non-bound proteins and low pH elution buffer was used to dissociate the bound antigen from the antibody. The eluted proteins or equal amounts of total proteins from human serum were boiled in Roti-Load1 Buffer (Carl Roth GmbH) by heating for 5 minutes at 100° C. Proteins were separated on SDS-polyacrylamide gels and transferred to PVDF membranes. The membranes were incubated overnight at 4° C. with primary antibodies: mouse anti-human uromodulin antibody (diluted 1:1000, Euroimmun), mouse anti-IL-1β antibody (diluted 1:1000, Cell Signaling) or rabbit anti-TNFα antibody (diluted 1:1000, Cell Signaling) and then with secondary anti-mouse HRP-conjugated antibody (diluted 1:2000, Santa Cruz Biotechnology) or anti-rabbit HRP-conjugated antibody (diluted 1:1000, Cell Signaling) for 1 hour at room temperature. The membranes were stripped in stripping buffer (Thermo Fisher Scientific) at room temperature for 10 min. Antibody binding was detected with ECL detection reagent (Thermo Fisher Scientific).

Calcium Phosphate Precipitation Assay

Calcium phosphate mineral phase formation assay was performed using a homogeneous system containing 10 mM $CaCl_2$ (Sigma-Aldrich) and 10 mM sodium phosphate buffer (pH7.4, Sigma Aldrich) in 500 mM HEPES buffer (pH7.4, Sigma Aldrich) in the presence of the indicated concentrations of native human uromodulin. After incubation for 10 minutes at room temperature, the samples were centrifuged at 1890 g for 30 seconds and the obtained pellet was dissolved in 150 mM HCl. Calcium levels were determined colorimetric by using QuantiChrom Calcium assay kit (BioAssay Systems) according to the manufacturer's protocol.

Hydroxyapatite Dissociation Assay

Hydroxyapatite dissociation assay was performed using a homogeneous system containing 2 mM hydroxyapatite nanoparticles (<200 nm particle size, Sigma Aldrich) in 500 mM HEPES buffer (pH7.4, Sigma Aldrich) in the presence of the indicated concentrations native human uromodulin. After overnight incubation at 37° C. on a shaker (100 rpm), the samples were centrifuged at 1890 g for 30 seconds and the obtained pellet was dissolved in 150 mM HCl. The calcium levels in the supernatant and the pellet, respectively, were determined colorimetric by using QuantiChrom Calcium assay kit (BioAssay Systems) according to the manufacturer's protocol.

Human Samples

All patients and volunteers gave informed consent. Blood was collected from patients of various stages of CKD to obtain serum. Healthy volunteers served as controls. Uromodulin levels were measured by ELISA (Euroimmun). Serum calcification propensity was analysed by determining the one-half maximal transition time ($T_{50}$) of in-vitro transformation from primary to secondary calciprotein particles by using a Nephelostar Plus nephelometer (BMG Labtech, Ortenberg, Germany). Where indicated, uromodulin was added to the serum samples.

Statistics

Data are shown as scatter dot plots and arithmetic mean±SEM. Normality was tested with Shapiro-Wilk test. Non-normal datasets were transformed (log, reciprocal or sqrt) prior to statistical testing to provide normality according to Shapiro-Wilk test. Statistical testing was performed by one-way Anova followed by Tukey-test for homoscedastic data or Games-Howell test for heteroscedastic data. Non-normal data were tested by the Steel-Dwass method. The Steel test and Dunett test, according to normality distribution, were used for the experiments of TNFα and IL-1β treatment. Two groups were compared by unpaired two-tailed t-test. For correlation analysis, Spearman correlation test was performed. $P<0.05$ was considered statistically significant.

EXAMPLES

Example 1: Uromodulin Supplementation is Able to Abolish Vascular Calcification

Figure 2:
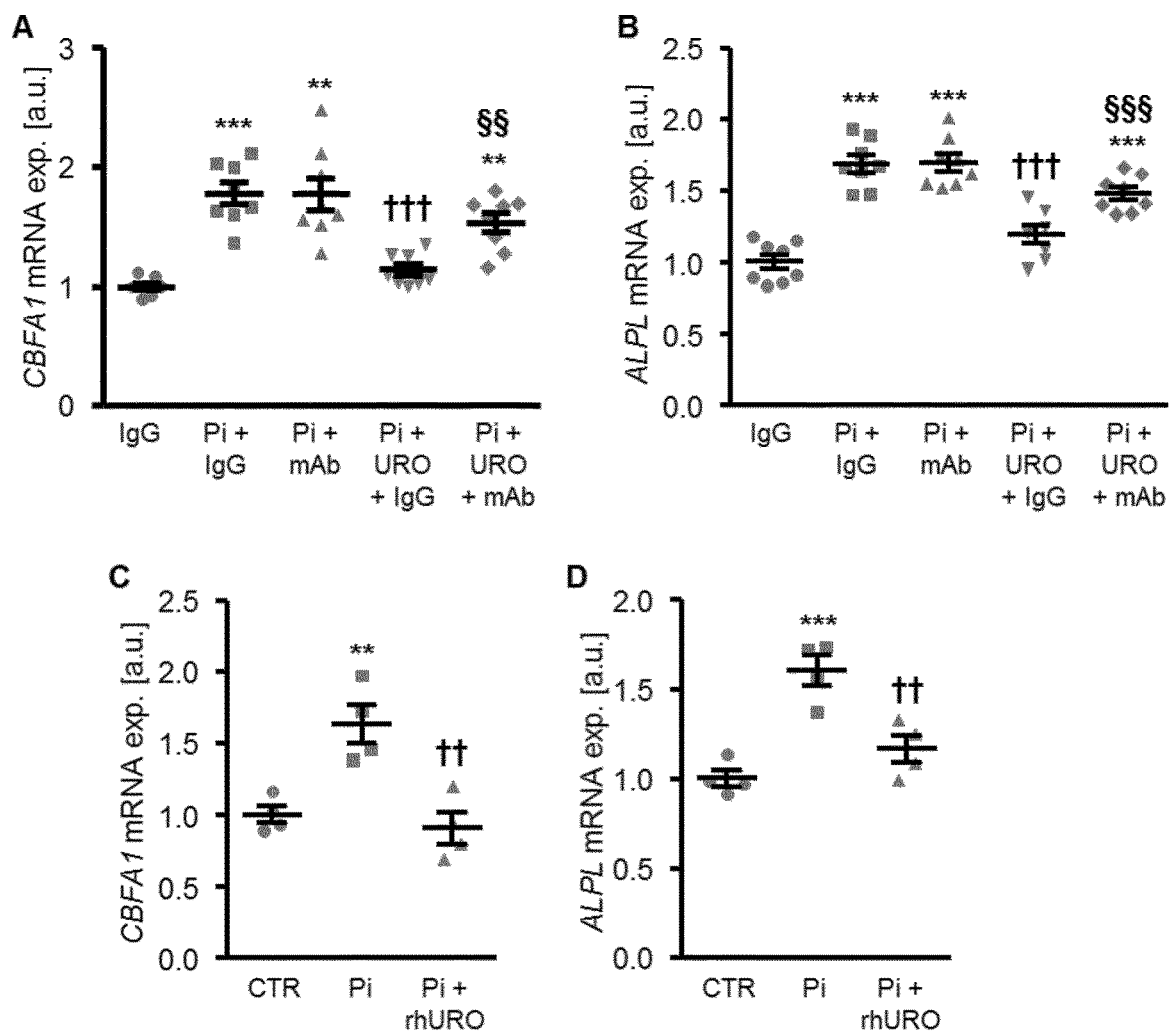
FIG. 2 A,B. Scatter dot plots and arithmetic means±SEM (n=8; arbitrary units, a.u.) of CBFA1 (A) and ALPL (B) relative mRNA expression in HAoSMCs following treatment for 24 hours with control or with 2 mM β-glycerophosphate (Pi) without or with additional treatment with 100 ng/ml native human uromodulin (URO) and with mouse monoclonal antibody against human uromodulin (mAb) or negative control mouse IgG (IgG). *($p<0.05$), ($p<0.01$), *($p<0.001$) statistically significant vs. IgG treated HAoSMCs; †($p<0.05$), †††($p<0.001$) statistically significant vs. HAoSMCs treated with IgG and Pi; §§ ($p<0.01$), ††† ($p<0.001$) statistically significant between HAoSMCs treated with Pi+URO+IgG and Pi+URO+mAb. C,D. Scatter dot plots and arithmetic means±SEM (n=4; a.u.) of CBFA1 (C) and ALPL (D) relative mRNA expression in HAoSMCs following treatment for 24 hours with control or with 2 mM β-glycerophosphate (Pi) without or with additional treatment with 100 ng/ml recombinant human uromodulin (rhURO). ($p<0.01$), *($p<0.001$) statistically significant vs. control treated HAoSMCs; ††($p<0.01$) statistically significant vs. HAoSMCs treated with Pi alone.

Uromodulin supplementation is able to prevent the osteoinductive properties of phosphate. Treatment even with low concentrations of uromodulin is able to inhibit osteogenic transformation of primary human aortic smooth muscle cells in-vitro (FIG. 1; FIG. 2). The osteoblastic transformation is evaluated as the relative increase of core-binding factor alpha 1 (CBFA1) and tissue non-specific alkaline phosphatase (ALPL) expression as well as of ALPL activity. This powerful effect cannot be replicated by treatment with serum albumin as control (FIG. 1). Moreover, this effect can be suppressed by an anti-uromodulin blocking antibody (FIG. 2). Therefore, uromodulin exerts powerful effects to prevent osteoinductive transformation of vascular smooth muscle cells.

Most importantly, uromodulin is able to prevent vascular calcification. Treatment with uromodulin completely prevents the calcification of the primary human aortic smooth muscle cells induced by calcification medium (FIG. 1). These experiments reflect the calcification processes in vascular tissue. Therefore, uromodulin treatment is a potent antagonist of vascular calcification.

Figure 3:
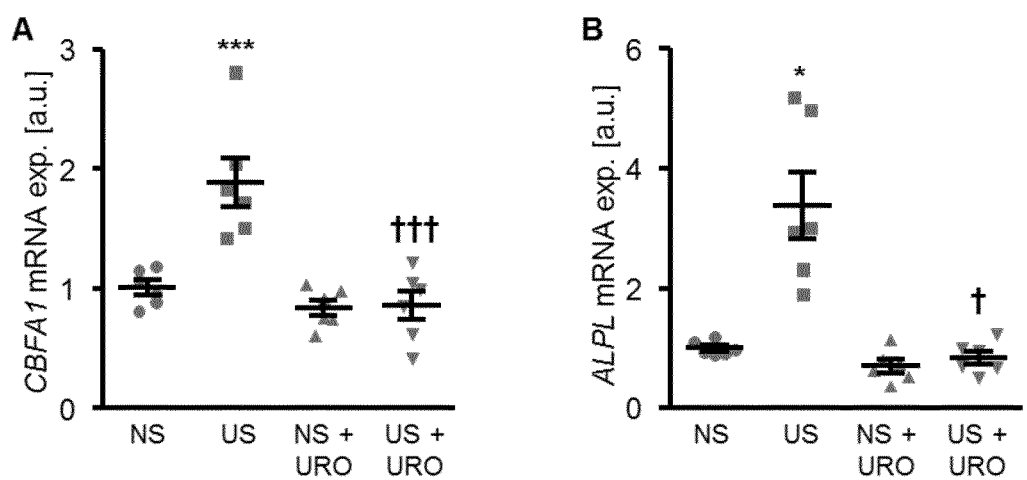
FIG. 3 A,B. Scatter dot plots and arithmetic means±SEM (n=6; arbitrary units, a.u.) of CBFA1 (A) and ALPL (B) relative mRNA expression in HAoSMCs following treatment for 24 hours with 15% normal serum (NS) or uremic serum (US) without or with additional treatment with 100 ng/ml native human uromodulin (URO). *($p<0.05$), *** ($p<0.001$) statistically significant vs. NS treated HAoSMCs; †($p<0.05$), †††($p<0.001$) statistically significant vs. respective serum treated HAoSMCs.

Uromodulin treatment is also able to inhibit primary human aortic smooth muscle cells osteogenic transformation induced during uremic conditions (FIG. 3). Thus, uromodulin may reduce the progression of vascular calcification triggered by complex conditions such as chronic kidney disease.

Figure 5:
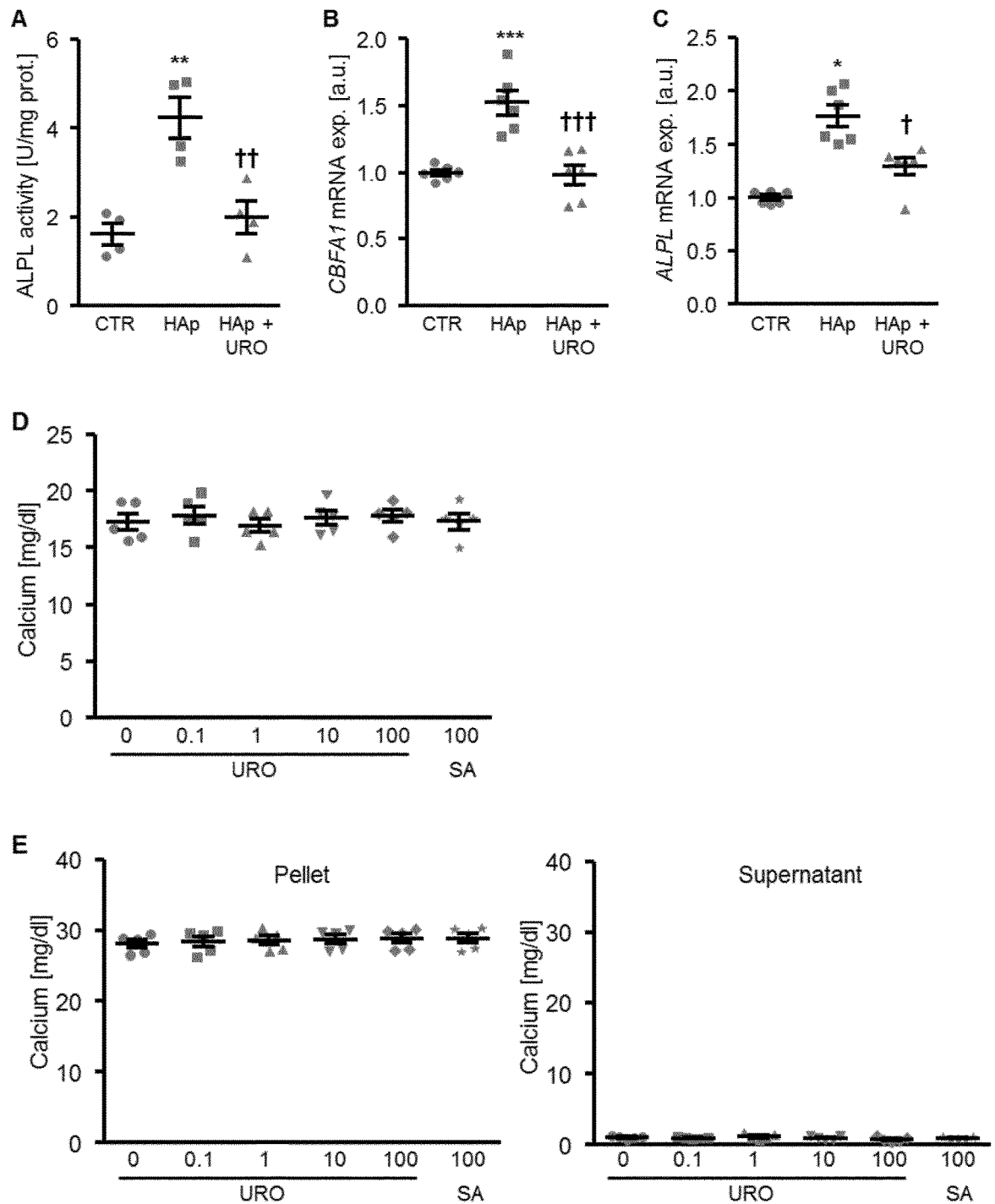
FIG. 5 A. Scatter dot plots and arithmetic means±SEM (n=4, U/mg protein) of alkaline phosphatase activity in HAoSMCs following treatment for 7 days with control or with 5 μg/ml hydroxyapatite (HAp) without or with additional treatment with 100 ng/ml native human uromodulin (URO) or 100 ng/ml serum albumin (SA). B,C. Scatter dot plots and arithmetic means±SEM (n=6; arbitrary units, a.u.) of CBFA1 (B) and ALPL (C) relative mRNA expression in HAoSMCs following treatment for 24 hours with control or with 5 µg/ml hydroxyapatite (HAp) without or with additional treatment with 100 ng/ml native human uromodulin (URO) or 100 ng/ml serum albumin (SA). *($p<0.05$), ($p<0.01$), *($p<0.001$) statistically significant vs. control treated HAoSMCs; †($p<0.05$), ††($p<0.01$), †††($p<0.001$) statistically significant vs. HAoSMCs treated with HAp alone. D. Scatter dot plots and arithmetic means±SEM (n=5; mg/dl) of calcium levels in the precipitated pellet following calcium phosphate precipitation in the presence of the indicated concentrations of native human uromodulin (URO, 0-100 ng/ml) or 100 ng/ml serum albumin (SA). E. Scatter dot plots and arithmetic means±SEM (n=5; mg/dl) of calcium levels in the pellet and supernatant, respectively, following hydroxyapatite nanoparticle dissociation in the presence of the indicated concentrations of native human uromodulin (URO, 0-100 ng/ml) or 100 ng/ml serum albumin (SA).

Uromodulin treatment is also able to inhibit primary human aortic smooth muscle cells osteogenic transformation induced by pre-formed hydroxyapatite crystals (FIG. 5). Therefore, uromodulin inhibits vascular calcification not by simple inhibition of calcium and phosphate precipitation, but by an active effect on vascular smooth muscle cells.

Example 2: Uromodulin Supplementation is Able to Inhibit Vascular Inflammation

Figure 4:
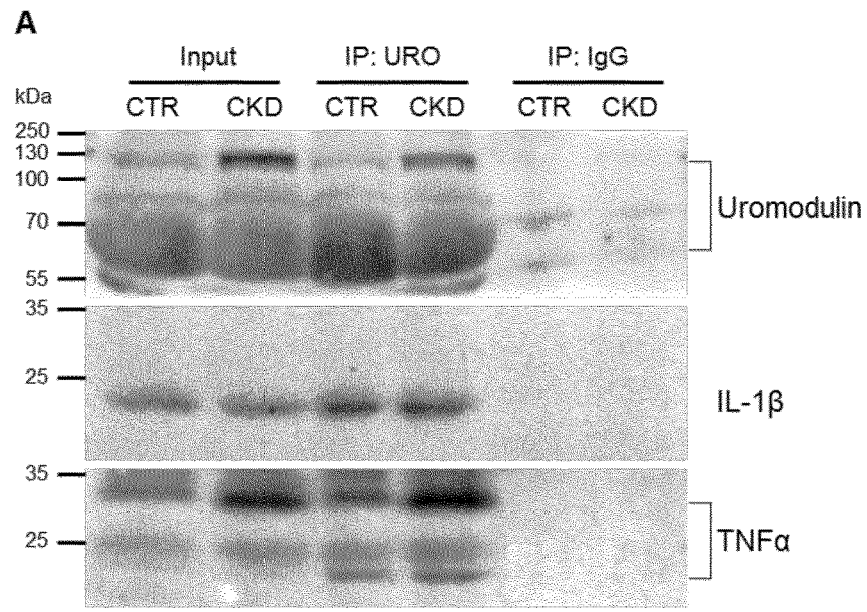
FIG. 4 A. Representative original Western blots (n=4) of uromodulin, IL-1β and TNFα protein expression in total serum (Input) and in uromodulin or negative control IgG immunoprecipitated samples of human serum collected from hemodialysis patients before dialysis (CKD) and from healthy volunteers (CTR). B,C. Scatter dot plots and arithmetic means±SEM (arbitrary units, a.u.) of NF-kB-dependent transcriptional activity measured by luciferase reporter assay in HAoSMCs following transfection for 48 hours with NF-kB-responsive luciferase/Renilla constructs and treatment for 30 min with 10 ng/ml IL-1β (B, n=6) or with 10 ng/ml TNFα (C, n=8) and without or with additional treatment with indicated concentrations of native human uromodulin (URO, 0-100 ng/ml) or 100 ng/ml serum albumin (SA). *($p<0.05$), ($p<0.01$) statistically significant vs. control treated HAoSMCs; †($p<0.05$) statistically significant vs. HAoSMCs treated with IL-11/TNFα alone. D. Scatter dot plots and arithmetic means±SEM (n=4; a.u.) of NF-kB-dependent transcriptional activity measured by luciferase reporter assay in HAoSMCs following transfection for 48 hours with NF-kB-responsive luciferase/Renilla constructs and treatment for 24 hours with control or with 2 mM 3-glycerophosphate (Pi) without or with additional treatment with 100 ng/ml native human uromodulin (URO) or 100 ng/ml serum albumin (SA). ($p<0.01$), ***($p<0.001$) statistically significant vs. control treated HAoSMCs; ††($p<0.00$) statistically significant vs. HAoSMCs treated with Pi alone. E. Representative confocal microscopy images (n=3) showing NF-kB p65 protein expression and localization in HAoSMCs following treatment for 24 hours with control or with 2 mM β-glycerophosphate (Pi) without or with additional treatment with 100 ng/ml native human uromodulin (URO) or 100 ng/ml serum albumin (SA). NF-kB p65 expression: green labeling, nuclei: purple labeling. Scale bar: 25 μm.
Figure 4:
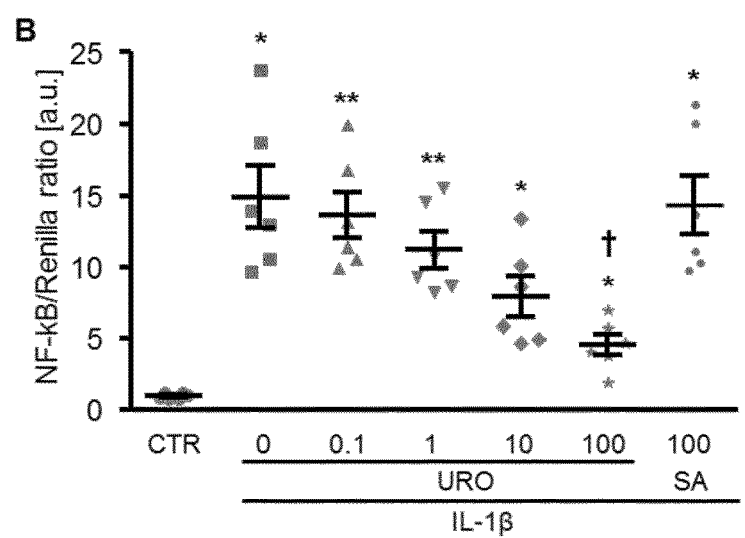
Figure 4:
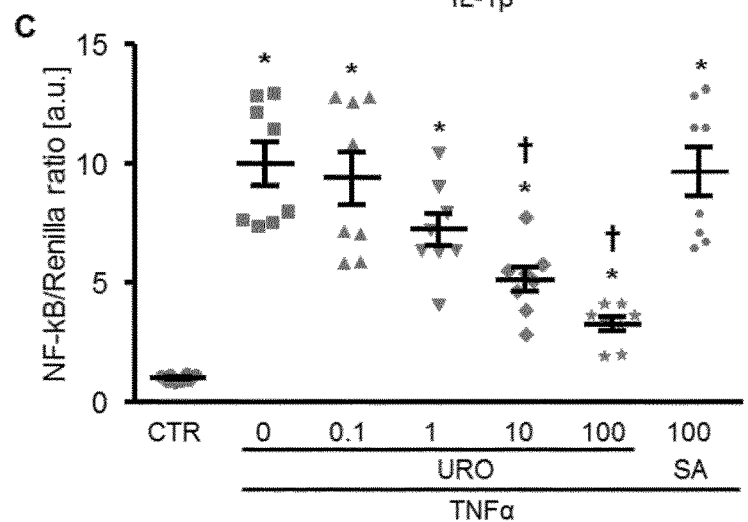

Uromodulin acts on vascular smooth muscle cells to inhibit vascular inflammation. Treatment with uromodulin inhibits activation of the "nuclear factor kappa-light-chain-enhancer of activated B cells" induced by pro-calcific environment (FIG. 4). This effect is specific to uromodulin and cannot be replicated by serum albumin as control. Therefore, uromodulin may be used to prevent vascular inflammation.

Uromodulin is able to counter the effects of inflammatory cytokines. Uromodulin presumably inactivates the effects of the pro-inflammatory cytokines tumor necrosis factor alpha (TNFα) and Interleukin 1 beta (IL-1β) (FIG. 4). Therefore, uromodulin can be used as an inhibitor of inflammation.

Serum uromodulin is able to interact with endogenous inflammatory cytokines TNFα and IL-1β in the serum from human patients, as shown by detection of these cytokines in uromodulin immunoprecipitated serum samples (FIG. 4).

One particular use where the treatment according to the invention is of benefit is the amelioration of inflammatory processes triggered by or associated with TNFα or IL-1β.

Figure 8:
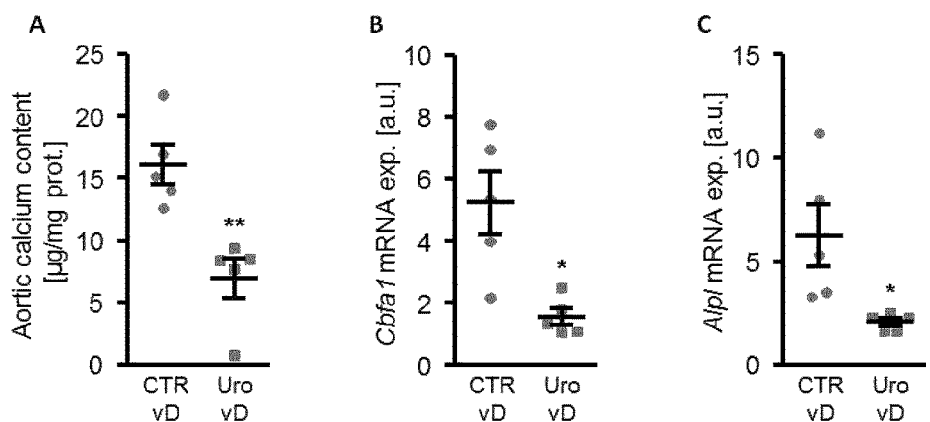
FIG. 8 A. Scatter dot plots and arithmetic means±SEM (n=5; µg/mg protein) of calcium content in the aortic arch from mice treated with AAV8-GFP as control (CTR) or with AAV8-mouse uromodulin (Uro) and additional treatment with high-dosed cholecalciferol (vD). B,C. Scatter dot plots and arithmetic means±SEM (n=5, arbitrary units, a.u.) of Cbfa1 (B) and Alpl (C) relative mRNA expression in aortic tissue from mice treated with AAV8-GFP as control (CTR) or with AAV8-mouse uromodulin (Uro) and additional treatment with high-dosed cholecalciferol (vD). *($p<0.05$), **($p<0.01$) statistically significant vs. CTR+vD treated mice.

Example 3: Uromodulin Overexpression is Able to Reduce Vascular Calcification In-Vivo Uromodulin overexpression is able to reduce aortic calcification and aortic osteogenic markers expression following high-dosed cholecalciferol treatment in mice (FIG. 8). Uromodulin overexpression shows anti-calcific effects in the vascular tissues without significantly affecting plasma calcium or phosphorus concentrations in the cholecalciferol treated mice (Table 1).

TABLE 1

Arithmetic means ± SEM of plasma calcium and phosphate in mice treated with AAV8-GFP as control (CTR) or with AAV8- mouse uromodulin (Uro) and additional treatment with high-dosed cholecalciferol (vD).

|  | CTR vD | Uro vD | |
|---|---|---|---|
| Calcium [mg/dl] | 18.51 ± 0.19 | 18.08 ± 0.54 | n = 5 |
| Phosphate [mg/dl] | 5.92 ± 0.11 | 5.89 ± 0.16 | n = 5 |

Figure 6:
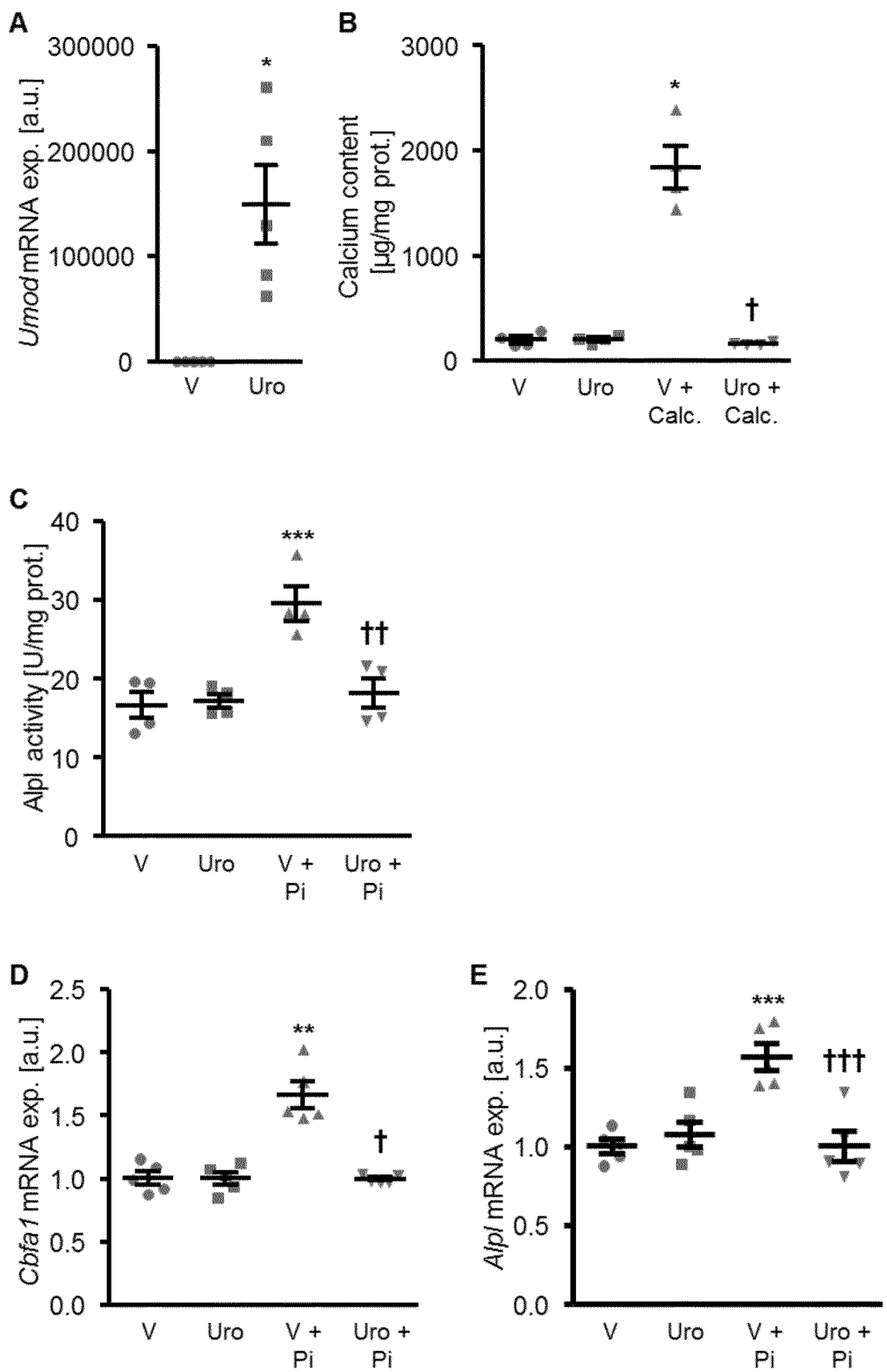
FIG. 6 A. Scatter dot plots and arithmetic means±SEM (n=5; arbitrary units, a.u.) of Umod relative mRNA expression in MOVAS cells following transfection for 48 hours with empty vector (V) or with a construct encoding mouse uromodulin (Uro). B. Scatter dot plots and arithmetic means±SEM (n=4, µg/mg protein) of calcium content in HAoSMCs following transfection for 11 days with empty vector (V) or with a construct encoding mouse uromodulin (Uro) and treatment with control or with calcification medium (Calc., 10 mM β-glycerophosphate+1.5 mM $CaCl_2$)). C. Scatter dot plots and arithmetic means±SEM (n=4, U/mg protein) of alkaline phosphatase activity in HAoSMCs following transfection for 7 days with empty vector (V) or with a construct encoding mouse uromodulin (Uro) and treatment with control or with 2 mM 3-glycerophosphate (Pi). D,E. Scatter dot plots and arithmetic means±SEM (n=5; a.u.) of Cbfa1 (D) and Alpl (E) relative mRNA expression in MOVAS cells following transfection for 48 hours with empty vector (V) or with a construct encoding mouse uromodulin (Uro) and treatment for 24 hours with control or with 2 mM 3-glycerophosphate (Pi). *($p<0.05$), ($p<0.01$), *($p<0.001$) statistically significant vs. V transfected MOVAS cells; †($p<0.05$), ††($p<0.01$), †††($p<0.001$) statistically significant vs. V transfected and Calc./Pi treated MOVAS cells.
Figure 7:
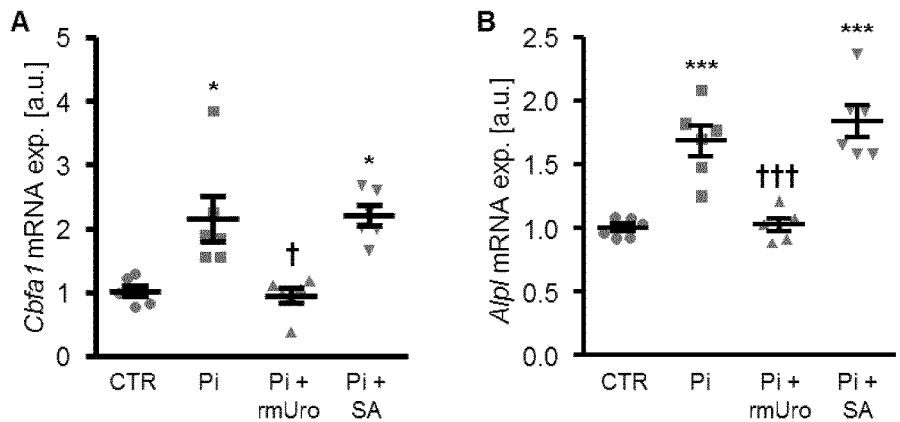
FIG. 7 Scatter dot plots and arithmetic means±SEM (n=6; arbitrary units, a.u.) of Cbfa1 (A) and Alpl (B) relative mRNA expression in MOVAS cells following treatment for 24 hours with control or with 2 mM β-glycerophosphate (Pi) without or with additional treatment with 100 ng/ml recombinant mouse uromodulin (rmUro). *($p<0.05$), *** ($p<0.001$) statistically significant vs. control treated MOVAS cells; †($p<0.05$), †††($p<0.001$) statistically significant vs. MOVAS cells treated with Calc./Pi alone.

These results were also confirmed in mouse smooth muscle cells in vitro. Uromodulin overexpression is able to prevent phosphate-induced calcification and osteoinductive signaling in MOVAS mouse aortic smooth muscle cells (FIG. 6). Similarly, uromodulin supplementation is able to prevent the osteoinductive properties of phosphate in MOVAS cells (FIG. 7).

Figure 9:
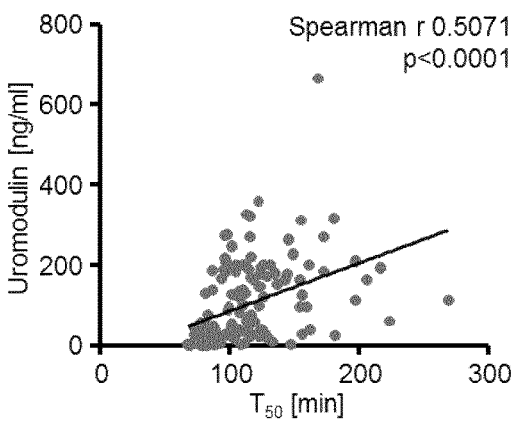
FIG. 9 A Scatter dot plot of correlation between serum uromodulin concentrations (ng/ml) and serum calcification propensity measured as calciprotein particle maturation time (T50, min) in human patients with CKD (n=138). P values are indicated in the figure.

Example 4: Serum Uromodulin Levels are Inversely Correlated with Serum Calcification Propensity in Chronic Kidney Disease Patients Serum uromodulin levels are inversely correlated with serum calcification propensity, a marker for increased risk for vascular calcification, in a chronic kidney disease patient cohort with various stages of renal disease (FIG. 9). Addition of exogenous uromodulin is not able to significantly modify the serum calcification propensity in controls or dialysis patients (Table 2), suggesting that uromodulin has no ex-vivo effects on overall propensity for calcification in serum but acts indirectly via other mechanisms.

TABLE 2

Arithmetic means ± SEM of serum calcification propensity measured as calciprotein particle maturation time ($T_{50}$) in the absence or presence of 100 ng/ml native human uromodulin (URO) in human hemodialysis patients before dialysis and in healthy volunteers.

|  | $T_{50}$ [min] | $T_{50}$ [min] (URO) | |
|---|---|---|---|
| CTR | 191.50 ± 9.74 | 212.62 ± 22.08 | n = 13 |
| CKD | 105.76 ± 16.32** | 122.46 ± 17.59* | n = 13 |

*($p < 0.05$),
**($p < 0.01$) statistically significant vs. control patients.

The inventors, thus, have substantiated the utility of uromodulin supplementation for the treatment and prevention of vascular calcification and its sequelae.

Similarly, the data presented herein substantiate the utility of uromodulin supplementation by any route to prevent inflammation, vascular calcification and its sequelae, cardiac dysfunction and hypertrophy, renal inflammation and decline of renal function as well as treatment of general inflammation.

The treatment with uromodulin is ideal for the use in human patients. Uromodulin is an endogenous protein produced in the human body. Under diseased state, especially chronic kidney disease, the body does not produce enough uromodulin. Therefore, uromodulin deficiency seems to be a cause for the progression of vascular calcification. Supplementation with uromodulin reduces vascular calcification. As it is an endogenous protein, supplementation should not be associated with any adverse effects.

The invention claimed is:

1. A method for treating vascular calcification or a disease caused by, or related to, vascular calcification, in a patient in need thereof, said method comprising administering to said patient an effective amount of a uromodulin polypeptide, wherein the patient is characterized by a peripheral uromodulin level below 125 ng/ml.

2. The method according to claim 1, wherein said uromodulin peptide comprises the polypeptide sequence set forth as SEQ ID NO: 1.

3. The method according to claim 1, wherein vascular calcification is associated with chronic kidney disease, diabetes, aging or atherosclerosis.

4. The method according to claim 1, wherein the patient is characterized by a peripheral uromodulin level below 100 ng/ml.

5. A method for treating vascular inflammation associated with vascular calcification, in a patient in need thereof, said method comprising administering to said patient an effective amount of a uromodulin polypeptide wherein the patient is characterized by a peripheral uromodulin level below 125 ng/ml.

6. The method according to claim 5, wherein said uromodulin peptide comprises the polypeptide sequence set forth as SEQ ID NO: 1.

7. The method according to claim 5, wherein the vascular inflammation associated with vascular calcification is associated with chronic kidney disease, diabetes, aging or atherosclerosis.

8. The method according to claim 5, wherein the patient is characterized by a peripheral uromodulin level below 100 ng/ml.

9. The method according to claim 5, wherein the uromodulin peptide is a recombinant peptide.

* * * * *